United States Patent [19]

Webb et al.

[11] Patent Number: 4,584,393

[45] Date of Patent: Apr. 22, 1986

[54] BIS(AMINOALKYL)DISILOXANES AND METHOD AND INTERMEDIATES FOR THEIR PREPARATION

[75] Inventors: Jimmy L. Webb, Ballston Lake; Cathryn E. Olsen, Ballston Spa, both of N.Y.

[73] Assignee: General Electric Company, Schenectady, N.Y.

[21] Appl. No.: 691,293

[22] Filed: Jan. 14, 1985

[51] Int. Cl.$^4$ .............................................. C07F 7/10
[52] U.S. Cl. ..................................... 556/407; 556/425
[58] Field of Search ................................ 556/425, 407

[56] References Cited

U.S. PATENT DOCUMENTS

| | | | |
|---|---|---|---|
| 2,754,311 | 7/1956 | Elliott | 556/425 |
| 3,045,036 | 7/1962 | Jex et al. | 556/425 |
| 3,803,196 | 4/1974 | Holub et al. | 556/425 |
| 4,152,346 | 5/1979 | Seiler et al. | 556/425 X |

FOREIGN PATENT DOCUMENTS

| | | | |
|---|---|---|---|
| 0734952 | 5/1966 | Canada | 556/407 |
| 1203776 | 10/1964 | Fed. Rep. of Germany | 556/407 |

*Primary Examiner*—Paul F. Shaver
*Attorney, Agent, or Firm*—William H. Pittman; James C. Davis, Jr.; James Magee, Jr.

[57] ABSTRACT

Bis(aminoalkyl)disiloxanes such as 1,9-diamino-4,4,6,6-tetramethyl-5-oxa-4,6-disilanonane are prepared by contacting an acyclic olefinic silazane such as 2-methyl-2-sila-3-aza-5-hexene with a hydrosilation catalyst to form an intermediate which is then hydrolyzed. When certain olefinic silazanes are hydrosilated with a reaction product of a platinum compound with an olefinic siloxane, the intermediate is a composition comprising novel cyclic silazanes such as 1,1-dimethyl-1-sila-2-azacyclopentane.

19 Claims, 4 Drawing Figures

(I) 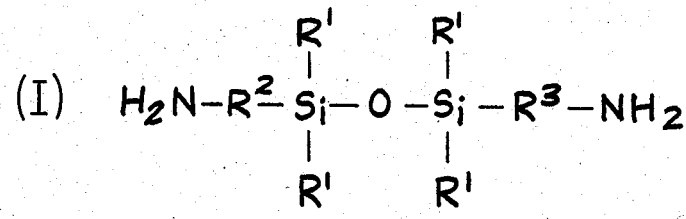
(II) 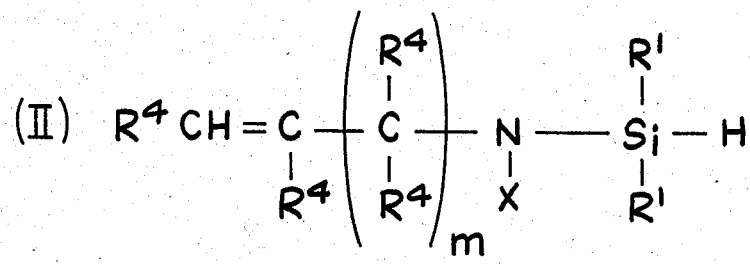
(III) 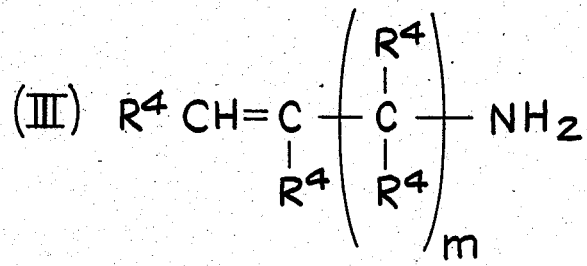
(IV) 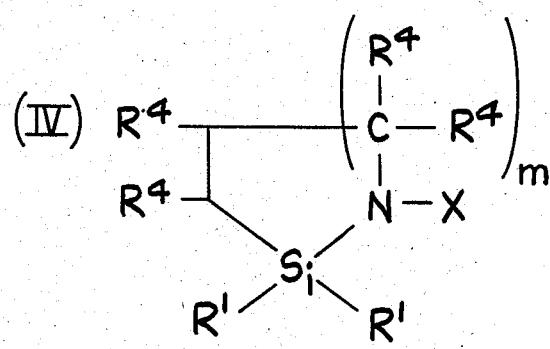

BIS(AMINOALKYL)DISILOXANES AND METHOD AND INTERMEDIATES FOR THEIR PREPARATION

This invention relates to the preparation of bis(aminoalkyl)disiloxanes, and more particularly to an improved method for preparing such compounds and intermediates used in said method.

Bis(aminoalkyl)disiloxanes are useful in many applications including the preparation of polyimides, especially polyetherimides such as those prepared by reaction with such dianhydrides as 2,2-bis[4-(3,4-dicarboxyphenoxy)phenyl]propane dianhydride ("bisphenol A dianhydride"). A particularly valuable bis(aminoalkyl)disiloxane used for this purpose is 1,9-diamino-4,4,6,6-tetramethyl-5-oxa-4,6-disilanonane, also known as bis(3-aminopropyl)tetramethyldisiloxane and bis(γ-aminopropyl)tetramethyldisiloxane. Commercial utilization of these compounds, however, has been inhibited by the lack of convenient methods for their preparation on a large scale. Previous methods for their preparation have involved a large number of complex and expensive reactions and/or processing steps.

A principal object of the present invention, therefore, is to provide a new method for the preparation of bis(aminoalkyl)disiloxanes.

A further object is to provide a preparative method which is convenient and relatively inexpensive.

A still further object is to provide novel chemical intermediates which are useful in said method.

Other objects will in part be obvious and will in part appear hereinafter.

In one of its aspects, the present invention is directed to a method for preparing bis(aminoalkyl)disiloxanes having formula I in the drawings, wherein $R^1$ is a $C_{1-4}$ primary or secondary alkyl radical, phenyl or substituted phenyl and each of $R^2$ and $R^3$ is an alkylene radical containing about 1–20 carbon atoms or a $C_{6-10}$ aryl-substituted derivative thereof, which comprises the steps of:

(A) contacting at least one acyclic olefinic mono- or disilazane of formula II, wherein each $R^4$ is independently hydrogen, a $C_{1-4}$ primary or secondary alkyl radical, phenyl or substituted phenyl, X is H or $SiH(R^1)_2$ and m is from 1 to about 18, with a hydrosilation catalyst to form an intermediate; and (B) hydrolyzing said intermediate.

As is apparent from formula I, the bis(aminoalkyl)disiloxanes prepared by the method of this invention include symmetrical and non-symmetrical compounds, according as $R^2$ and $R^3$ are identical or different. The $R^1$ values therein may be phenyl radicals; substituted phenyl radicals such as tolyl, chlorophenyl, carbomethoxyphenyl or cyanophenyl; or (preferably) $C_{1-4}$ primary or secondary alkyl radicals such as methyl, ethyl, 1-propyl, 2-propyl, 1-butyl, 2-butyl and 2-methyl-1-propyl. Methyl and ethyl radicals, especially methyl, are particularly preferred.

Each of $R^2$ and $R^3$ is an alkylene radical which may contain one or more phenyl or substituted phenyl substituents of the type described hereinabove with reference to $R^1$. They are preferably lower alkylene radicals (i.e., radicals containing up to 7 carbon atoms) or substituted derivatives thereof, especially those in which 2–4 carbon atoms separate the nitrogen atom from the silicon atom in formula I. Illustrative radicals of this type are ethylene, propylene, trimethylene, phenylethylene, 1-phenyltrimethylene, 2-phenyltrimethylene, -phenethylethylene, 1,2-butylene and the like.

The ethylene, propylene and trimethylene radicals are preferred, especially the latter. Thus, the method of this invention is particularly useful for the preparation of the aforementioned 1,9-diamino-4,4,6,6-tetramethyl-5-oxa-4,6-disilanonane and its isomers 1,8-diamino-2,3,3,5,5-pentamethyl-4-oxa-3,5-disilaoctane and 1,7-diamino-2,3,3,5,5,6-hexamethyl-4-oxa-3,5-disilaheptane. As described hereinafter, these three compounds are often obtained in the form of mixtures.

Step A of the method of this invention is the hydrosilation of at least one acyclic olefinic mono- or disilazane of formula II. In that formula, the $R^4$ values are usually all hydrogen. Any of them may, however, be phenyl, substituted phenyl or $C_{1-4}$ primary or secondary alkyl radicals such as those described hereinabove, with the same preferences. It should be noted that the present invention contemplates the use of compounds wherein all $R^4$ values are the same, as well as compounds wherein they are all different. This includes compounds in which m is from 2 to about 18 (although m is preferably 1) and all of the $R^4$ substituents on the resulting alkylene radical are different. The silazane may be a monosilazane, wherein X is H, or a disilazane, wherein X is $SiH(R^1)_2$. The monosilazanes are preferred since they yield substantially pure bis(aminoalkyl)disiloxanes rather than mixtures, as explained hereinafter.

The mono- and disilazanes of formula II may be prepared by known methods such as the reaction of an olefinic amine of formula III with a chlorosilane of the formula $(R^1)_2SiHCl$ in the presence of an acid acceptor such as excess olefinic amine, as disclosed, for example, in Example 12 of U.S. Pat. No. 3,642,854, the disclosure of which is incorporated by reference herein. Suitable olefinic amines include allylamine (which is preferred), methallylamine and 3-butenylamine. The preferred chlorosilane is dimethylchlorosilane.

The product of the olefinic amine-chlorosilane reaction is monosilazane, disilazane or a mixture thereof, depending on various factors such as the molar ratio of the reactants. The preferred reactant in step A is the substantially pure monosilazane. Purification may be effected by conventional means such as distillation and column chromatography.

Hydrosilation catalysts useful in step A are those known in the art. They are typically platinum catalysts in which the platinum may be present in elemental or chemically combined (i.e., divalent or tetravalent) form. Illustrative hydrosilation catalysts are platinum supported on substantially inert substrates such as aluminum or silica gel; platinum compounds such as $Na_2PtCl_4$, $K_2PtCl_4$, $H_2PtCl_6$ and alkylplatinum halides; and siloxyorganosulfur-platinum or aluminoxyorganosulfur-platinum compositions of the type disclosed in copending, commonly assigned application Ser. No. 527,538, filed Aug. 29, 1983, the disclosure of which is incorporated by reference herein.

Preferably, however, the hydrosilation catalyst is formed by the reaction of a platinum compound with at least one olefinic siloxane, as disclosed in the following U.S. Pat. Nos.

3,419,593
3,715,334
3,775,452
3,814,730
4,288,345.

The disclosures of these patents are incorporated by reference herein. Particularly useful as the reaction products of platinum compounds, especially chloroplatinic acid and hydrates thereof, with 3,3,5,5-tetramethyl-3,5-disila-4-oxa-1,6-heptadiene. The amount of hydrosilation catalyst used is usually such as to provide an amount of platinum equal to about 10–400 ppm. (by weight) based on the olefinic amine.

Step A may be conveniently conducted by heating the mixture of the olefinic amine and hydrosilation catalyst at a temperature in the range of about 75°–125° C., preferably in a substantially inert organic solvent. Suitable solvents include aliphatic hydrocarbons such as n-hexane and petroleum naphtha, aromatic hydrocarbons such as benzene and toluene, ethers such as ethyl ether, tetrahydrofuran and dioxane, and aprotic polar solvents such as dimethyl sulfoxide. The hydrosilation reaction is often conveniently conducted under pressure, such as by employing a closed vessel.

The molecular structure of the product of step A depends on the molecular structure of the silazane and the hydrosilation catalyst used. According to Example 12 of the aformentioned U.S. Pat. No. 3,642,854, the use of a solution of $H_2PtCl_6$ in isopropanol results in the formation of a "viscous, non-distillable polymer". Polymeric intermediates are also obtained according to the present invention when various hydrosilation catalysts are used, and also when m is greater than 2. It has been discovered, however, that the products obtained by using the above-described reaction products of platinum compounds with olefinic siloxanes in which m is 1 or 2 are compositions comprising at least one cyclic silazane of formula IV, wherein $R^1$, $R^4$ and X are as previously defined and m is 1 or 2. The preparation of such cyclic silazane compositions by the action of a hydrosilation catalyst prepared from a platinum compound and 3,3,5,5-tetramethyl-3,5-disila-4-oxa-1,6-heptadiene 2-methyl-2-sila-3-aza-5-hexane and mixtures thereof with 2-methyl-3-dimethylsilyl-2-sila-3-aza-5-hexene has been confirmed by analysis as described hereinafter. The cyclic disilazanes [i.e., the compounds of formula IV wherein X is $SiH(R^1)_2$] are apparently derived from the acyclic olefinic disilazanes (the corresponding compounds of formula II). Compositions comprising cyclic mono- and disilazanes of formula IV are another aspect of the invention.

If desired, the cyclic silazanes formed in step A may be isolated and/or purified by conventional techniques. However, isolation is usually not necessary.

In step B, the intermediate formed in step A is hydrolyzed. Hydrolysis is conveniently and simply effected by heating the intermediate, which may remain in solution in the solvent used in step A, with an excess of water at a temperature within the range of about 75°–105°0 C. until the reaction is complete. Especially when conducted on a large scale, the hydrolysis reaction may be strongly exothermic and it may be necessary to control it by adding water slowly or incrementally. In general, cyclic disilazanes are hydrolyzed much more slowly than the corresponding monosilazanes.

The molecular structures of the bis(aminoalkyl)disiloxanes obtained by the method of this invention have been found to vary according to the nature of the acyclic olefinic silazanes used in step A. For example, substantially pure 1,9-diamino-4,4,6,6-tetramethyl-5-oxa-4,6-disilanonane may be obtained from substantially pure 2-methyl-2-sila-3-aza-5-hexene (the monosilazane of formula II wherein each $R^1$ is methyl, each $R^4$ is hydrogen, X is hydrogen and m is 1). On the other hand, the product obtained from unpurified monosilazane or a mixture of the monosilazane with 2-methyl-3-dimethylsilyl-2-sila-3-aza-5-hexene (the corresponding disilazane of formula II wherein X is dimethylsilyl) may be a mixture of the isomeric compounds recited hereinabove, which constitute another aspect of the invention.

The analyses of the intermediates and products obtained according to this invention were conducted by a combination of gas chromatography and mass spectrography. The gas chromatography was performed using a Varian Model 3700 chromatograph equipped with a J&W Scientific Type DB-1 glass capillary column, 30 meters in length and having an internal diameter of 0.25 mm. and a film thickness of 0.10 mm. The pressure across the capillary column was reduced with a 1/50-volume gas splitter, with the volume being made up at the end of the column before the detector. The inlet pressure was 12 psi. of helium. Thermal programming was maintained at −20° C. for 2 minutes, and then increased by 5° per minute to a final temperature of 300° C. Sample size was 0.5 microliter.

Under these conditions, the following retention times were observed:

| Compound | Retention time, sec. |
| --- | --- |
| 2-methyl-2-sila-3-aza-5-hexene | 800 |
| 2-methyl-2-dimethylsilyl-2-sila-3-aza-5-hexene | 1250 |
| 1,1-Dimethyl-1-sila-2-azacyclopentane | 941 |
| 1,1-Dimethyl-2-dimethylsilyl-1-sila-2-azacyclopentane | 1330 |
| 1,9-Diamino-4,4,6,6-tetramethyl-5-oxa-4,6-disilanonane | 2250 |

The method of this invention is illustrated by the following examples.

EXAMPLE 1

A pressure vessel was charged with one liter of an unpurified hexane solution of a mixture of 98.9% 2-methyl-2-sila-3-aza-5-hexene and 1.1% 2-methyl-3-dimethylsilyl-2-sila-3-aza-5-hexene, and there was added 3.3 ml. of a hydrosilation catalyst prepared from chloroplatinic acid and 3,3,5,5-tetramethyl-3,5-disila-4-oxa-1,6-heptadiene by the method disclsoed in Example 10 of U.S. Pat. No. 3,814,730, said catalyst containing 5% platinum. The vessel was sealed and heated at 100° C. for 4 hours, whereupon hydrosilation occured. The product was identified by analysis (as described hereinabove) as a mixture of 2-methyl-2-sila-3-aza-5-hexene and 2-methyl-3-dimethylsilyl-2-sila-3-aza-5-hexene.

A mixture of the hexane solution of the hydrosilation intermediate and excess water was heated for 24 hours at 100° C. The hexane was then removed by distillation and the residue was distilled under vacuum. The product was shown by analysis to be a mixture of 1,9-diamino-4,4,6,6-tetramethyl-5-oxa-4,6-disilanonane, 1,8-diamino-2,3,3,5,5-pentamethyl-4-oxa-3,5-disilaoctane and 1,7-diamino-2,3,3,5,5,6-hexamethyl-4-oxa-3,5-disilaheptane. It was reacted with bisphenol A dianhydride to form a polyetherimide having tensile strength and elongation properties identical to those of the corresponding product prepared from pure 1,9-diamino-4,4,6,6-tetramethyl-5-oxa-4,6-disilanonane.

EXAMPLE 2

The procedure of Example 1 was repeated, using 2-methyl-2-sila-3-aza-5-hexene which had been passed through silica gel to remove impurities. The product obtained was substantially pure 1,9-diamino-4,4,6,6-tetramethyl-5-oxa-4,6-disilanonane.

EXAMPLES 3–5

The cyclization reaction of Example 1 was repeated using the following hydrosilation catalysts in substantially the same proportions:

Example 3—an aluminum sphere-supported platinum catalyst, commercially available from Engelhard Minerals & Chemical Co.

Example 4—the reaction product of chloroplatinic acid with a γ-mercaptopropyltrimethoxysilane-functionalized silica gel, prepared as described in Example 1 of the aforementioned application Ser. No. 527,538.

Example 5—trimethylplatinum iodide tetramer.

In Example 3 the silazane solution was passed through silica gel to remove impurities and by-products before catalyst addition. The cyclization products in all three examples were predominantly cyclic disilazane and hydrolysis was very slow; in Example 4, its was stopped before completion. The principal hydrolysis product obtained in Example 3 was 1,9-diamino-4,4,6,6-tetramethyl-5-oxa-4,6-disilanonane; in Example 5, a product mixture similar to that of Example 1 was obtained.

What is claimed is:

1. A method for preparing bis(aminoalkyl)disiloxanes having formula I in the drawings, wherein $R^1$ is a $C_{1-4}$ primary or secondary alkyl radical, phenyl or substituted phenyl and each of $R^2$ and $R^3$ is an alkylene radical containing about 1–20 carbon atoms or a $C_{6-10}$ aryl-substituted derivative thereof, which comprises the steps of:
   (A) contacting at least one acyclic olefinic mono- or disilazane of formula II, wherein each $R^4$ is independently hydrogen, a $C_{1-4}$ primary or secondary alkyl radical, phenyl or substituted phenyl, X is H or $SiH(R^1)_2$ and m is from 1 to about 18, with a hydrosilation catalyst to form an intermediate; and
   (B) hydrolyzing said intermediate.

2. A method according to claim 1 wherein m is 1 or 2 and each of $R^2$ and $R^3$ is a lower alkylene or substituted lower alkylene radical.

3. A method according to claim 2 wherein each $R^4$ is hydrogen and m is 1.

4. A method according to claim 3 wherein the hydrosilation catalyst is formed by the reaction of a platinum compound with at least one olefinic siloxane.

5. A method according to claim 4 wherein $R^1$ is methyl.

6. A method according to claim 5 wherein X is H.

7. A method according to claim 5 wherein a mixture of cyclic silazanes in which X is H and $SiH(R^1)_2$ is used in step A.

8. A method according to claim 5 wherein the hydrosilation catalyst is a reaction product of a platinum compound with 3,3,5,5-tetramethyl-3,5-disila-4-oxa-1,6-heptadiene.

9. A method according to claim 8 wherein the platinum compound is chloroplatinic acid or a hydrate thereof.

10. A method according to claim 9 wherein X is H.

11. A method according to claim 9 wherein a mixture of cyclic silazanes in which X is H and $SiH(R^1)_2$ is used in step A.

12. A method according to claim 5 wherein step B is conducted by heating the intermediate formed in step A with an excess of water at a temperature within the range of about 75°–105° C.

13. A method according to claim 12 wherein X is H.

14. A method according to claim 12 wherein a mixture of acyclic silazanes in which X is H and $SiH(R^1)_2$ is used in step A.

15. A composition comprising a mixture of cyclic silazanes having formula IV in the drawings, wherein $R^1$ is a $C_{1-4}$ primary or secondary alkyl radical or phenyl, $R^4$ is hydrogen, a $C_{1-4}$ primary or secondary alkyl radical or phenyl and m is 1 or 2; said mixture containing the monosilazane in which X is hydrogen and the disilazane in which X is $SiH(R^1)_2$.

16. A composition according to claim 15 wherein each $R^4$ is hydrogen and m is 1.

17. A composition according to claim 16 wherein $R^1$ is methyl.

18. A composition according to claim 17 wherein X is hydrogen.

19. A composition comprising a mixture of 1,9-diamino-4,4,6,6-tetramethyl-5-oxa-4,6-disilanonane, 1,8-diamino-2,3,3,5,5-pentamethyl-4-oxa-3,5-disilaoctane and 1,7-diamino-2,3,3,5,5,6-hexamethyl-4-oxa-3,5-disilaheptane.

* * * * *